US012616669B2

(12) United States Patent
    Pielak

(10) Patent No.:     US 12,616,669 B2
(45) **Date of Patent:        *May 5, 2026**

(54) METHODS AND CHEMICAL COMPOSITIONS FOR TREATING SKIN CONDITIONS BY PROVIDING LONG LASTING SKIN pH CONTROL FOR IMPROVING SKIN BARRIER FUNCTION

(71) Applicant: Soteri Skin, Inc., El Cerrito, CA (US)

(72) Inventor: Rafal M. Pielak, El Cerrito, CA (US)

(73) Assignee: Soteri Skin, Inc., El Cerrito, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/312,236

(22) Filed: Aug. 27, 2025

(65) Prior Publication Data

US 2026/0034083 A1      Feb. 5, 2026

Related U.S. Application Data

(63) Continuation of application No. 19/306,366, filed on Aug. 21, 2025, which is a continuation of application No. 19/091,737, filed on Mar. 26, 2025, now Pat. No. 12,396,973, which is a continuation-in-part of application No. 18/253,173, filed as application No. PCT/US2022/071895 on Apr. 25, 2022.

(60) Provisional application No. 63/766,313, filed on Mar. 3, 2025, provisional application No. 63/299,239, filed on Jan. 13, 2022, provisional application No. 63/179,998, filed on Apr. 26, 2021.

(51) Int. Cl.
    *A61K 36/00*     (2006.01)
    *A61K 9/00*     (2006.01)
    *A61K 9/06*     (2006.01)
    *A61K 31/191*     (2006.01)
    *A61K 31/194*     (2006.01)
    *A61K 31/196*     (2006.01)
    *A61K 31/198*     (2006.01)
    *A61K 31/201*     (2006.01)
    *A61K 31/4172*     (2006.01)
    *A61K 36/185*     (2006.01)
    *A61K 36/28*     (2006.01)
    *A61P 17/00*     (2006.01)
    *A61P 17/04*     (2006.01)

(52) U.S. Cl.
    CPC .......... *A61K 31/194* (2013.01); *A61K 9/0014* (2013.01); *A61K 9/06* (2013.01); *A61K 31/191* (2013.01); *A61K 31/196* (2013.01); *A61K 31/198* (2013.01); *A61K 31/201* (2013.01); *A61K 31/4172* (2013.01); *A61K 36/185* (2013.01); *A61K 36/28* (2013.01); *A61P 17/00* (2018.01); *A61P 17/04* (2018.01)

(58) Field of Classification Search
    None
    See application file for complete search history.

(56) References Cited

U.S. PATENT DOCUMENTS 12,396,973 B2 *   8/2025   Pielak .................. A61K 31/198

* cited by examiner

*Primary Examiner* — Russell G Fiebig
(74) *Attorney, Agent, or Firm* — Bajwa IP Law Firm

(57)               ABSTRACT

Provided are methods and composition for treating skin barrier functions and associated disorders. Formulated compositions may be applied on human skin to maintain a desired skin surface pH over an extended period of time without irritating the skin. Maintaining the desired surface pH aids in treatment of eczema, in addition to other skin conditions.

7 Claims, 9 Drawing Sheets

<u>100</u>

Maintaining a first pH buffer of at a target skin area for a first period of time by applying a first composition to the target skin area

~ 102

Maintaining a second pH buffer at the target skin area for a second period of time by applying a second composition to the target skin area

~ 104

202

Time (hours)

302  304

306  308

400

Time (hours)

502

504

602                                604

702                                                 704

802

804

METHODS AND CHEMICAL COMPOSITIONS FOR TREATING SKIN CONDITIONS BY PROVIDING LONG LASTING SKIN pH CONTROL FOR IMPROVING SKIN BARRIER FUNCTION

CROSS-REFERENCE TO RELATED APPLICATIONS

This application is a continuation of U.S. patent application Ser. No. 19/306,366, filed on Aug. 21, 2025, which is a continuation of U.S. patent application Ser. No. 19/091,737, filed on Mar. 26, 2025, which claims priority from U.S. Provisional Patent Application No. 63/766,313, filed Mar. 3, 2025, entitled "Chemical Composition Providing Long Lasting Skin pH Control for Improving Skin Barrier Function and Treatment of Skin Barrier Disorders," and is a continuation-in-part of U.S. patent application Ser. No. 18/253,173, filed May 16, 2023, entitled "Chemical Composition Providing Long Lasting Skin pH Control for Improving Skin Barrier Function and Treatment of Skin Barrier Disorders", which is nation stage filing of PCT/US22/71895 filed Apr. 25, 2022, entitled "Chemical Composition Providing Long Lasting Skin pH Control for Improving Skin Barrier Function and Treatment of Skin Barrier Disorders", which claims priority to both U.S. Provisional Patent Application No. 63/299,239, filed Jan. 13, 2022, and U.S. Provisional Patent Application No. 63/179,998, filed Apr. 26, 2021, and additionally claims priority from U.S. Provisional Patent Application No. 63/766,313, filed Mar. 3, 2025, entitled "Chemical Composition Providing Long Lasting Skin pH Control for Improving Skin Barrier Function and Treatment of Skin Barrier Disorders." which are all incorporated herein by reference in their entireties.

FIELD

The present disclosure relates generally to skin topical compositions and formulations, and more specifically to method of application of topical formulations and topical formulations designed to maintain optimal skin surface pH over an extended period of time.

BACKGROUND

The formation of lipophilic components of Stratum Corneum (SC) involves several pH-dependent enzymes. Two key lipid-processing enzymes, beta-glucocerebrosidase and acidic sphingomyelinase, have pH optima of 5.6 and 4.5, respectively. Both lipid-processing enzymes are involved in the synthesis of ceramides, which are critical components of the permeability barrier.

Optimal skin surface pH does not only influence the barrier homeostasis, but also affects SC integrity, cohesion, and desquamation. An elevated pH increases the activity of serine proteases, kallikrein 5 and 7, which are involved in the desquamation and degradation of corneodesmosomes.

Acidic pH is also essential for normal skin flora growth, whereas pathogenic bacteria, such as *Staphylococcus aureus*, thrives at a neutral pH level. A number of factors, including both endogenous and exogenous elements, affect skin pH.

Various studies have shown that elevations of pH in normal skin create a disturbed barrier, linked to increased activity of serine proteases and reduced activities of ceramide-generating enzymes. Therefore, changes in skin pH greatly affect skin function and skin health, as well as contribute to a number of skin conditions, such as atopic dermatitis, eczema, rosacea, psoriasis, and acne.

BRIEF SUMMARY

This summary is intended to provide an overview of the subject matter of the present disclosure, and is not intended to identify essential elements or key elements of the subject matter, nor is it intended to be used to determine the scope of the claimed implementations. Its sole purpose is to present some concepts of one or more exemplary aspects in a simplified form as a prelude to the more detailed description that is presented later. The proper scope of the present disclosure may be ascertained from the claims set forth below in view of the detailed description below and the drawings.

One or more exemplary embodiments describe an exemplary method for treating eczema, comprising maintaining a first pH buffer at a target skin area between 4.5 and 5.5 for a first period of time by applying a first composition to the target skin area, the first composition with a first buffer capacity concentration of acids and conjugate bases, the target skin area comprising surface of skin currently or previously indicating symptoms of eczema, the first period of time comprising at least five days, and wherein the applying the first composition comprising applying the first composition over the at least five days at least twice daily. In an exemplary embodiment, the first composition may comprise a first agent comprising citric acid, sodium citrate, or combination thereof, comprising 0.3-1.5% weight composition of the first composition, and comprising pKa of 3.13, 4.76, or 6.0, gluconic acid comprising 0.1-0.5% weight composition of the first composition, the gluconic acid comprising pKa of 3.7, glutamic acid comprising 0.1-0.5% weight composition of the first composition, the gluconic acid comprising pKa of 2.19 and 4.25, aspartic acid comprising 0.1-0.5% weight composition of the first composition, the gluconic acid comprising pKa of 1.88 and 3.65, and histidine comprising 0.1-2.0% weight composition of the first composition, the gluconic acid comprising pKa of 6. The first composition may further comprise a second agent, comprising shea butter comprising 8.5% weight composition of the first composition, the shea butter comprising oleic acid, stearic acid, palmitic acid, and linoleic acid with a pKa of 4.5, and free fatty acid content of 1 percent, and sunflower oil comprising 7% weight composition of the first composition, the sunflower oil comprising linoleic acid with a pKa of 4.5, and free fatty acid content of 1 percent. The first composition may further comprise a third agent, comprising amino acid, peptide mix, or combination thereof, comprising 0.1-2% weight composition of the first composition, the third agent with a range of pKa between 1.82 and 10.7. In an exemplary embodiment, first composition third agent may have a range of pKa between 4 and 6.

An exemplary method may further include maintaining a second pH buffer at the target skin area between 4.5 and 4.9 for a second period of time by applying a second composition to the target skin area, the second composition with a second buffer capacity concentration of second composition acids and second composition conjugate bases, the second buffer capacity more than the first buffer capacity, wherein the applying the second composition comprising applying the second composition to the target skin area at least twice daily.

In an exemplary embodiment, the second composition may comprise a second composition first agent, comprising citric acid and sodium citrate comprising 1.5-15% weight composition of the second composition, gluconic acid comprising 0.1-1.0% weight composition of the second composition, glutamic acid comprising 0.1-1.0% weight composition of the second composition, aspartic acid comprising 0.1-1.0% weight composition of the second composition, and histidine comprising 0.1-2.0% weight composition of the second composition, wherein the second pH-adjusting agent comprising pKa of 3.13, 4.76, or 6.

In an exemplary embodiment, the second composition may further comprise a a second composition second agent, comprising shea butter comprising 8.7% weight composition of the second composition, the shea butter comprising oleic acid, stearic acid, palmitic acid, and linoleic acid with a pKa of 4.5, and free fatty acid content of 1% weight composition of the second composition, and sunflower oil comprising 6.5% weight composition of the second composition, the sunflower oil comprising linoleic acid with a pKa of 4.5, and free fatty acid content of 1 percent.

In an exemplary embodiment, an exemplary second composition may further include a second composition third agent, comprising amino acid, peptide mix, or combination thereof, comprising 0.1-5% weight composition of the second composition, the second composition third agent with a range of pKa between 1.82 and 10.7. In an exemplary embodiment, second composition third agent may have a range of pKa between 3.5 and 5.5.

This Summary is provided to introduce a selection of concepts in a simplified form; these concepts are further described below in the Detailed Description. This Summary is not intended to identify key features or essential features of the claimed subject matter, nor is it intended to be used to limit the scope of the claimed subject matter.

DESCRIPTION OF THE FIGURES

The present application can be understood by reference to the following description taken in conjunction with the accompanying figures.

DETAILED DESCRIPTION

All illustrations, drawings, visual aid and/or figures accompanying the following document are for the purpose of describing the present invention and are not intended to limit the scope of the present invention.

In some aspects, provided are exemplary topical formulations that may maintain optimal skin surface pH levels over an extended period of time. In some embodiments, exemplary topical formulation maintains the skin surface pH level at around 4.7 for an extended period of time. In an exemplary embodiment, keeping skin surface pH level allows for reduction and prevention of skin conditions, including eczema. In an exemplary embodiment, exemplary formulations sustain a strong pH buffer capacity on an exemplary skin surface allowing for maintaining a pH level for an extended period of time, including six to twelve hours. As such, applying exemplary formulations provide constant maintenance of a pH level around 4.7 on an exemplary skin surface, allowing for reduction and prevention of eczema. In an exemplary embodiment, exemplary formulations maintain an exemplary buffer capacity while not irritating an exemplary skin surface. Accordingly, exemplary formulations may remain primarily on an exemplary skin surface to exert their buffering effect and diffuse slowly through an exemplary stratum coronium to establish a graduation pH gradient.

In an exemplary embodiment, exemplary formulations may allow for key enzymatic reactions and processes such as ceramide production. For example, in exemplary embodiments, exemplary topical formulations may support the function of beta-glucocerebrosidase and acid sphingomyelinase. In an exemplary embodiment, exemplary topical formulations' pH level may further support the skin microbiome. In an exemplary embodiment, exemplary topical compositions may be formulated as creams. In additional exemplary embodiments, exemplary compositions may further be formulated as creams, lotions, serums, cleanser, toners, foundations, and/or similar.

In an exemplary embodiment, exemplary compositions may be provided in form of an exemplary tube, an exemplary container, or another physical medium configured to hold and disperse and exemplary composition.

Figure 1:
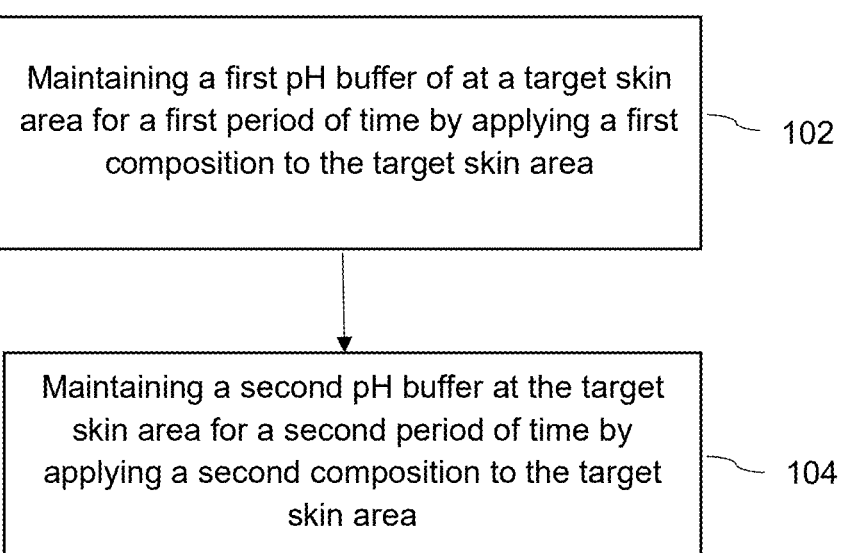
FIG. 1 is a flowchart of a method for treating eczema, consistent with one or more exemplary embodiments of the present disclosure.

In an exemplary embodiment, FIG. 1 is a flowchart of a method 100 for treating eczema, consistent with one or more exemplary embodiments of the present disclosure.

In an exemplary embodiment, method 100 may comprise step 102, which may comprise maintaining a first pH buffer at a target skin area. In an exemplary embodiment, the first pH buffer may be maintained between 4.2 to 5.2, 4.4 and 5.0, or at or around 4.7 pH. In an exemplary embodiment, maintaining the first pH buffer may comprise applying a first composition to the target skin area. In an exemplary embodiment, the first composition may comprise a first buffer capacity concentration of acids and conjugate bases.

In an exemplary embodiment, the target skin area may comprise surface of skin currently or previously indicating symptoms of eczema. In an exemplary embodiment, exemplary eczema symptom may comprise one or more of redness, itching, inflammation, dryness, and scaling.

In an exemplary embodiment, the first composition may be applied for a first period of time. In an exemplary embodiment, an exemplary first period of time may comprise at least five days, two weeks, a time period between two to four weeks, or more than four weeks. In an exemplary embodiment, the applying may comprise applying the first composition at least at an average of once daily or twice daily over the first period of time. In an exemplary embodiment, the applying may comprise applying the first composition at least twice daily so that at each application an exemplary pH level is applied to a skin surface until an exemplary first buffer capacity and additional conditions allow. In an exemplary embodiment, an exemplary period of time may be extended, and may take into account a specific period of time along with reduction in symptoms, for example, it may comprise three weeks of regular application and reduction in amount of inflammation and redness.

In an exemplary embodiment, an exemplary first composition may comprise one or more of an anti-inflammatory agents, pH-adjusting agents, and stabilizing agents.

In an exemplary embodiment, a first exemplary agent may comprise a PH-adjusting agent and an exemplary anti-inflammatory agent. In an exemplary embodiment, a first exemplary agent may comprise shea butter and sunflower oil. In an exemplary embodiment, the shea butter may comprise 8-9% weight composition of the first composition. In an exemplary embodiment, the shea butter may comprise oleic acid, stearic acid, palmitic acid, and linoleic acid, wherein the linoleic acid may have a pKa of 4.5. In an exemplary embodiment, the shea butter may comprise a free fatty acid content of 1 percent.

In an exemplary embodiment, the sunflower oil may comprise 6-8% weight composition of the first composition. In an exemplary embodiment, the sunflower oil may comprise linoleic acid with a pKa of 4.5. In an exemplary embodiment, the sunflower oil may comprise a free fatty acid content of 1 percent.

In an exemplary embodiment, an exemplary second agent may be a pH-adjusting agent may comprise citric acid, sodium citrate, or a combination thereof in an amount of citric acid comprising between 0.3 and 1.5% weight composition of the first composition, and sodium citrate, an exemplary conjugate based on citric acid, being a respective weight composition of the first composition based on amount of acid. In an exemplary embodiment, the citric acid and sodium citrate may comprise pKa values of 3.13, 4.76, and 6.0.

In an exemplary embodiment, the second agent may further comprise gluconic acid in an amount of between 0.1 and 0.5% weight composition of the first composition. In an exemplary embodiment, the gluconic acid may comprise a pKa of 3.7.

In an exemplary embodiment, the second agent may further comprise glutamic acid in an amount of between 0.1 and 0.5% weight composition of the first composition. In an exemplary embodiment, the glutamic acid may comprise pKa values of 2.19 and 4.25.

In an exemplary embodiment, the second agent may further comprise aspartic acid in an amount of between 0.1 and 0.5% weight composition of the first composition. In an exemplary embodiment, the aspartic acid may comprise pKa values of 1.88 and 3.65.

In an exemplary embodiment, the second agent may further comprise histidine in an amount of between 0.1 and 2.0% weight composition of the first composition. In an exemplary embodiment, the histidine may comprise a pKa of 6.0.

In an exemplary embodiment, propionic acid and sodium propionate may be included in an amount of between 0.1 and 0.5% weight composition. In an exemplary embodiment, these components may contribute to the acid mantle augmenting system.

In an exemplary embodiment, an exemplary third agent may comprise an exemplary pH-adjusting agent and/or an exemplary stabilizing agent. In an exemplary embodiment, an exemplary third agent may comprise an amino acid mix, a peptide mix, or a combination thereof. In an exemplary embodiment, an exemplary third agent may comprise an amino acids mix and may comprise between 0.1 to 2.0% weight composition of the first composition.

In an exemplary embodiment, xanthan gum may be present in an amount of between 0.2 and 0.8% weight composition. In an exemplary embodiment, the xanthan gum may function to maintain emulsion stability. In an exemplary embodiment, black tea extract may be included in an amount of between 4.5 to 5.5% weight composition. In an exemplary embodiment, the black tea extract may provide antioxidative properties through its polyphenol content.

In an exemplary embodiment, the first composition may comprise specific formulation aids. In an exemplary embodiment, cetearyl alcohol/ceteareth-20 may be present in an amount of between 7.3 to 8.3% weight composition to create a stable emulsion. In an exemplary embodiment, dimethicone may be included in an amount of between 1.2 to 1.8% weight composition to form a protective surface layer. In an exemplary embodiment, monolaurin may be present in an amount of between 0.2 to 0.8% weight composition to provide antimicrobial activity.

In an exemplary embodiment, the first composition may comprise a preservation system. In an exemplary embodiment, this system may include hexanediol/octanediol in an amount of between 0.4 to 1.0% weight composition and phenoxyethanol in an amount of between 0.2 to 0.8% weight composition.

In an exemplary embodiment, the first composition may comprise a solvent system. In an exemplary embodiment, the solvent may comprise purified water in an amount of 48 to 50 weight percentage, or may be specifically 49 weight percentage of the second composition. In an exemplary embodiment, this specific water content may optimize the delivery and performance of the active components.

In an exemplary embodiment, an exemplary solvent may comprise 20-50% weight composition in water-in-oil emulsion and 50-90% weight composition in oil-in-water emulsion.

In an exemplary embodiment, the method of applying the first composition may comprise specific application techniques designed to maximize therapeutic benefit. In an exemplary embodiment, the first composition may be applied to clean, slightly damp skin. In an exemplary embodiment, the application may comprise gentle, circular motions to ensure even distribution across the target skin area.

In an exemplary embodiment, the twice-daily application may comprise a morning application and an evening application. In an exemplary embodiment, the morning application may occur after cleansing and before exposure to environmental factors. In an exemplary embodiment, the evening application may occur after cleansing and as the final step in a skincare routine.

In an exemplary embodiment, a skin mimicking ceramide complex may be included in an amount of between 1.5 to 2.5% by weight, and colloidal oatmeal in an amount of between 1.2 to 1.8% by weight.

In an exemplary embodiment, the amount of first composition applied may depend on the size of the target skin area. In an exemplary embodiment, sufficient first composition may be applied to form a thin, even layer across the entire target area. In an exemplary embodiment, the application may continue until the composition is fully absorbed into the skin.

In an exemplary embodiment, the target skin area may be monitored for changes throughout an observation period. In an exemplary embodiment, visible improvements may begin to appear within five days within the first week of consistent application. In an exemplary embodiment, the improvements may comprise reduction in redness, decreased itching, or improved skin texture.

In an exemplary embodiment, the pH-adjusting agent components may work synergistically through their complementary pKa values to maintain the target pH range. In an exemplary embodiment, the combination of acids spanning pKa values from 1.88 to 6.0 may enable effective buffering capacity throughout the target pH range of 4.4 to 5.0. In an exemplary embodiment, this buffering system may be supported by the free fatty acids present in both the shea butter and sunflower oil components, which may contribute to overall pH maintenance while providing anti-inflammatory benefits.

In an exemplary embodiment, an exemplary first period of first composition application may prepare the skin for transition to the second composition. In an exemplary embodiment, the transition may be initiated when specific improvement markers are observed. In an exemplary embodiment, these markers may comprise reduced inflammation, improved skin barrier function, stabilized skin surface pH, and decreased frequency of flares.

In an exemplary embodiment, method 100 may further comprise step 104. In an exemplary embodiment, step 104 may comprise maintaining a second pH buffer at the target skin area. In an exemplary embodiment, the second pH buffer may be maintained between 4.5 and 4.9. In an exemplary embodiment, maintaining the second pH buffer may comprise applying a second composition to the target skin area. In an exemplary embodiment, the second composition may comprise a second buffer capacity concentration of acids and conjugate bases. In an exemplary embodiment, the second buffer capacity may be greater than the first buffer capacity described with respect to step 102.

In an exemplary embodiment, an exemplary second composition may comprise one or more of a second composition first agent, a second composition second agent, and a second composition third agent. In an exemplary these respective three agents may comprise pH-adjusting agents, anti-inflammatory agents, and stabilizing agents. In an exemplary embodiment, these components may work synergistically to maintain the narrower pH range required for the maintenance phase of treatment.

In an exemplary embodiment, the second composition first agent may comprise a pH adjusting agent and anti-inflammatory agent, which may comprise shea butter and sunflower oil. In an exemplary embodiment, the shea butter may comprise between 8 to 9% weight composition of the second composition. In an exemplary embodiment, the shea butter may comprise a specific combination of fatty acids. In an exemplary embodiment, these fatty acids may comprise oleic acid, stearic acid, palmitic acid, and linoleic acid. In an exemplary embodiment, the linoleic acid may have a pKa of 4.5. In an exemplary embodiment, the shea butter may maintain a free fatty acid content of 1 percent.

In an exemplary embodiment, the sunflower oil may comprise between 6.0 and 7.0% weight composition of the second composition. In an exemplary embodiment, the sunflower oil may comprise linoleic acid with a pKa of 4.5. In an exemplary embodiment, the sunflower oil may maintain a free fatty acid content of between 0.8 to 1.2 percent. In an exemplary embodiment, the combination of shea butter and sunflower oil at these specific concentrations may provide enhanced barrier support during the maintenance phase.

In an exemplary embodiment, the second composition second agent may comprise an pH-adjusting agent, which may comprise an enhanced buffer system. In an exemplary embodiment, this exemplary enhanced buffer system may comprise citric acid and sodium citrate in an amount of between 6.2 and 7.2% weight composition of the second composition. In an exemplary embodiment, this increased concentration, compared to the first composition, may provide stronger pH maintenance capacity. In an exemplary embodiment, citric aid may comprise between 1.2 and 2.2% and sodium citrate may comprise between 4.5 and 5.5% weight composition of the second composition.

In an exemplary embodiment, the second composition second agent pH may further comprise additional buffering components. In an exemplary embodiment, the pH-adjusting agent may include gluconic acid in an amount of between 0.1 to 0.5% weight composition of the second composition. In an exemplary embodiment, glutamic acid may be present in an amount of between 0.1 to 0.5% weight composition. In an exemplary embodiment, aspartic acid may be included in an amount of between 0.1 to 0.5% weight composition. In an exemplary embodiment, histidine may be present in an amount of between 0.1 to 0.5% weight composition. In an exemplary embodiment, these components may work together to maintain the desired pH range.

In an exemplary embodiment, the second composition second agent may comprise pKa values of 3.13, 4.76, and 6.0. In an exemplary embodiment, this pKa distribution may enable precise maintenance of the target pH range.

In an exemplary embodiment, propionic acid and sodium propionate may be included in an amount of between 0.1 to 0.5% % weight composition. In an exemplary embodiment, these components may maintain acid mantle augmentation during an exemplary maintenance phase.

In an exemplary embodiment, an exemplary second composition third agent may comprise an exemplary pH-adjusting agent of an exemplary stabilizing agent. In an exemplary embodiment, an exemplary second composition third agent may comprise an amino acid mix, a peptide mix, or a combination thereof. In an exemplary embodiment, an exemplary second composition third agent may comprise an amino acids mix and may comprise between 0.1 to 5.0% weight composition of the second composition.

In an exemplary embodiment, xanthan gum may be present in an amount of between 0.2 to 0.8% weight composition. In an exemplary embodiment, the xanthan gum may function to maintain emulsion stability during long-term use.

In an exemplary embodiment, the second composition may comprise specific formulation aids. In an exemplary embodiment, cetearyl alcohol/ceteareth-20 may be present in an amount of between 7.3 to 8.3% weight composition to maintain emulsion stability. In an exemplary embodiment, dimethicone may be included in an amount of between 0.07 to 1.3% weight composition to provide continued surface protection. In an exemplary embodiment, monolaurin may be present in an amount of between 0.2 to 0.8% weight composition to provide ongoing antimicrobial activity.

In an exemplary embodiment, the second composition may comprise additional therapeutic components. In an exemplary embodiment, niacinamide may be present in an amount of between 0.7 to 1.3% by weight of the second composition. In an exemplary embodiment, colloidal oat-meal may be included in an amount of between 0.7 to 1.3% by weight. In an exemplary embodiment, glycerin may be present in an amount of between 6.5 to 7.5% by weight. In an exemplary embodiment, a skin mimicking ceramide complex may be included in an amount of between 0.7 to 1.3% by weight.

In an exemplary embodiment, the second composition may comprise a solvent system. In an exemplary embodi-ment, the solvent may comprise purified water in an amount of 53 to 54 weight percentage, or may be specifically 53.5 weight percentage of the second composition. In an exem-plary embodiment, this specific water content may optimize the delivery and performance of the active components.

In an exemplary embodiment, an exemplary solvent may comprise 20-50% weight composition in water-in-oil emul-sion and 50-90% weight composition in oil-in-water emul-sion.

In an exemplary embodiment, the second composition may comprise a preservation system. In an exemplary embodiment, this system may include hexanediol/octanediol in an amount of between 0.4 to 1.0% weight composition and phenoxyethanol in an amount of between 0.2 to 0.8% weight composition.

In an exemplary embodiment, the transition from step 102 to step 104 may occur after specific criteria are met. In an exemplary embodiment, these criteria may comprise a cer-tain amount of time, such as continuous use of first com-position over 4 weeks or longer. Alternatively, exemplary specific criteria may be reduction in visible eczema symp-toms. In an exemplary embodiment, the symptom improve-ment may be assessed through reduction in several key indicators. In an exemplary embodiment, these indicators may include visible skin redness and the frequency and intensity of itching. In an exemplary embodiment, improve-ment may also be measured through reduction in visible inflammation. In an exemplary embodiment, surface dryness and the presence of scaling or flaking may also be evaluated when considering the transition timing. In an exemplary embodiment, specific criteria may mean that first composi-tion is applied to an exemplary target skin area and condition of exemplary skin is not worse than when an exemplary first composition started being applied, that is, the skin may have adjusted to acidity, and specifically buffer capacity within composition one and it may be applied without irritating the skin.

In an exemplary embodiment, the method of applying the second composition may comprise specific techniques. In an exemplary embodiment, these techniques may be adjusted from those used in step 102 to reflect the maintenance nature of the treatment. In an exemplary embodiment, once skin is adjusted to an exemplary first composition, an exemplary second composition with an enhanced buffer capacity may be utilized ensuring pH level is maintained for a longer period of time. In an exemplary embodiment, exemplary second composition allows for maintaining a desired pH level of target areas on skin at 4.7, or a range around 4.7 such as 4.6 to 4.8.

In an exemplary embodiment, the second composition may be applied with particular attention to previously affected areas. In an exemplary embodiment, the application may focus on areas that were targeted during step 102. In an exemplary embodiment, the application technique may emphasize even distribution of the enhanced buffer system to ensure consistent pH maintenance across all treated areas. Due to an enhanced buffer, impact to skin surface, such as water, acidity produced by skin, etc, may be fought off for a much longer time. In an exemplary embodiment, exem-plary compositions maintain this buffer for long period of time ranging from for more than 6 hours to more than 12 hours, without irritating the skin.

Accordingly, in exemplary embodiments, applying an exemplary second composition skin of a human, where the skin has a has a skin surface pH, allows a surface pH level to be maintained at around 4.7 for at least 6 hours.

In some embodiments, the topical formulations are pH optimized to match the skin surface pH for treatment of skin barrier function and associated disorders. Examples of such disorders or skin conditions include acne, psoriasis, rosacea, xerosis, and various forms of eczema including, for example, atopic dermatitis and contact dermatitis. In some embodiments, the topical formulations are pH optimized to treat different skin conditions resulting from dysregulated skin surface pH. In other embodiments, the topical formu-lations have optimized pH and pH buffer capacity to support wound healing (for example, chronic wounds such as in diabetes).

All of the listed exemplary skin conditions may either be consequences of a disrupted skin barrier or may result in skin barrier disruption. Consequently, improving an exem-plary skin barrier may aid in treatment. By maintaining skin surface pH, utilizing exemplary topical formulations pro-vided herein improve skin barrier function and consequently may provide improvements in skin conditions.

Figure 2A:
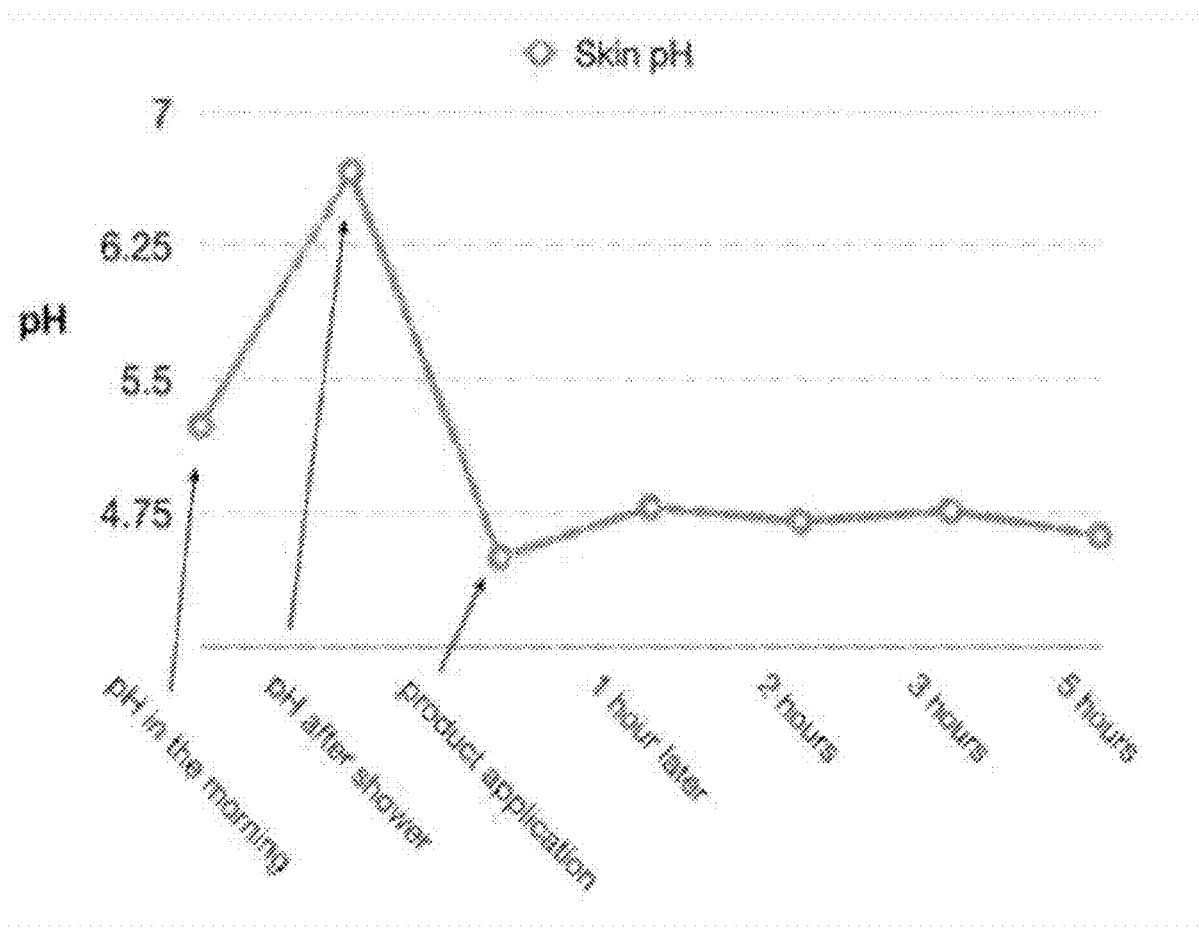
FIG. 2A is a graph of the stabilization of the pH skin level after topical application of an exemplary formulation provided herein, consistent with one or more exemplary embodiments of the present disclosure.
Figure 2B:
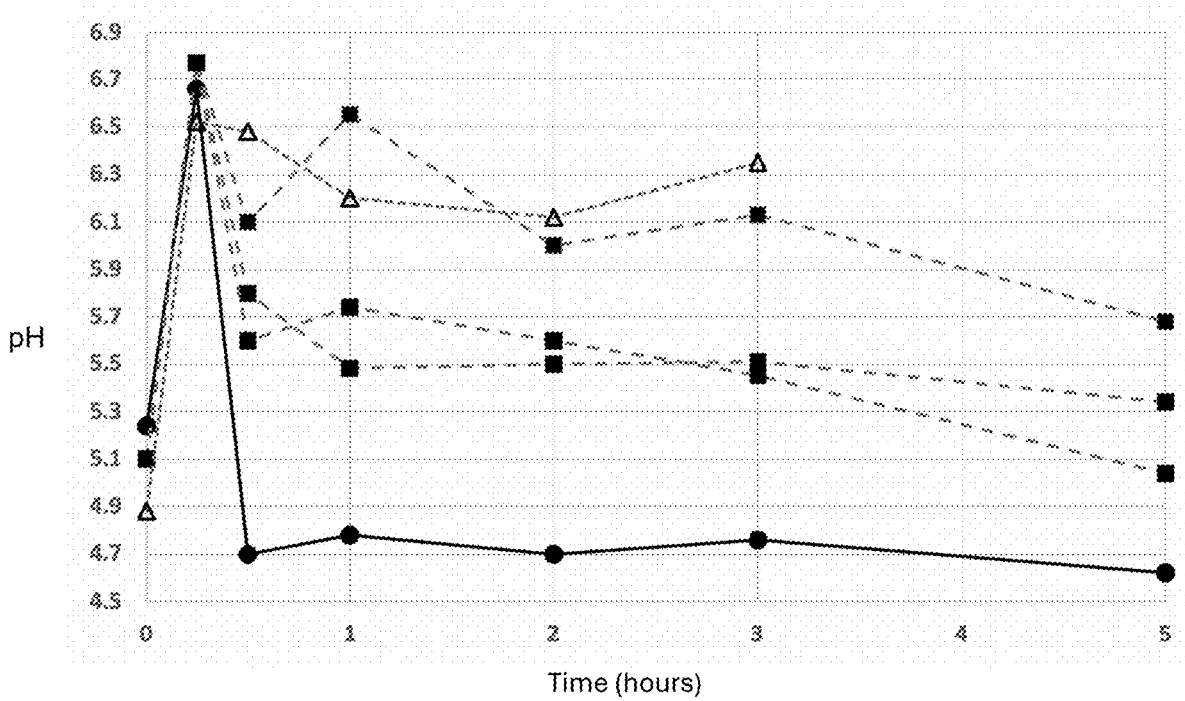
FIG. 2B is a graph comparing an exemplary formulation provided herein (solid line with circle markers) to three different topical creams commercially available on the market (dashed lines with square markers) and no product (dashed line with triangle markers) by measuring skin pH, consistent with one or more exemplary embodiments of the present disclosure.

In an exemplary embodiment, exemplary compositions and formulations maintain the skin surface pH level at a exemplary desired levels for key enzymatic reactions involved in the skin barrier synthesis and maintenance as seen in FIG. 2B. Maintaining the skin surface pH at the optimal pH level (e.g., pH around 4.7) may be better tolerated, safer, and have superior outcomes on skin health and treatment of skin disorders than temporary, acute acidi-fication with solutions adjusted to a pH well below the natural skin pH. Exemplary compositions provided herein may be formulated to maintain steady pH of the skin at the optimal level over at least 6 hours, at least 8 hours, or at least 12 hours, and prevent pH fluctuations, that is, their buffering capacity may allow for maintenance of a desired pH level on a surface of target skin for up to 12 hours. In an exemplary embodiment, exemplary formulations maintain a desire pH level without irritating the targe skin. In an exemplary embodiment, the desired pH level may be 4.4-5.0 or spe-cifically plus/minus 0.1 of 4.7.

In detail, in an exemplary embodiment, exemplary topical formulations provided may include a pH buffering system with strong buffer capacity around pH 4.7, the desired pH or natural pH of healthy skin. In some variations, the pH buffering system may include hydrogen ion acceptors and donors that have pKa values that span from pKa 3 to 5.5, optimally with at least one molecule with a pKa around 4.7. In an exemplary embodiment, an exemplary pH buffering system may include hydrogen ion acceptors and donors that do not readily diffuse through the skin, which would affect their concentration on the skin surface and consequently result in a pH shift over time. In an exemplary embodiment, exemplary pH buffering systems may not be irritating and may be well tolerated even for sensitive skin or skin affected by eczema or psoriasis.

In an exemplary embodiment, "around 4.7" in the context of pH or pKa in this application refers to 4.7+/−0.3.

Figure 3:
FIG. 3 displays various images of target skin areas pre and post application of exemplary formulations, consistent with one or more exemplary embodiments of the present disclosure.
Figure 3:
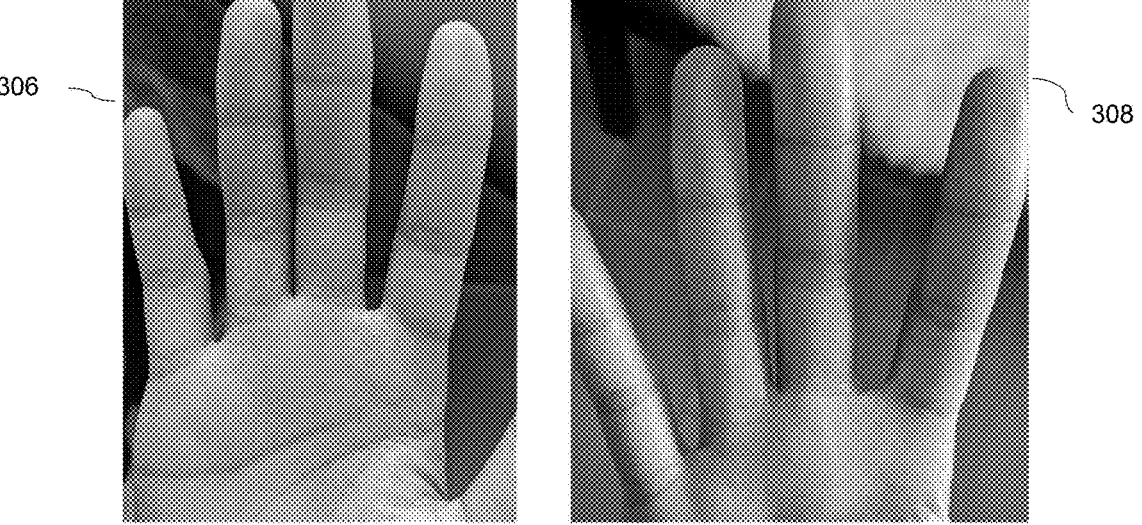

In an exemplary embodiment, provided herein are therapeutic effects of exemplary formulations, particularly for the treatment of dermatoses, such as eczema, as seen in FIG. 3.

FIG. 3 displays various images of target skin areas pre and post application of exemplary formulations, consistent with one or more exemplary embodiments of the present disclosure. In detail, image 302 displays a facial area before topical application of an exemplary formulation while image 304 displays the same facial area from image 302 after 11 days of consistent topical application of an exemplary formulation Similarly, image 306 displays a hand before topical application of an exemplary formulation, while image 308 displays the same hand as in image 306 after 14 days of consistent topical application of an exemplary formulation.

Traditional topical products containing water and oils (emulsions) typically contain preservatives that prevent microbial growth. Preservatives can be irritating for skin prone to dermatitis (eczema). In fact, preservatives are one of the most common sensitizers and irritants in contact dermatitis and atopic eczema. The topical formulations provided herein are self-preserving by combination of low pH, high ionic strength, and low water availability. This provides additional benefits in the treatment of skin affected by eczema or other forms of dermatitis.

The components and uses of the topical formulations provided herein are described in further detail below.

Components of an Exemplary Topical Formulation

Exemplary compositions provided herein are formulated for topical use on human skin. In an exemplary embodiment, provided is an exemplary topical composition with an optimal pH buffer capacity at around pH 4.7. In some embodiments, the topical composition, when applied to human skin, maintains a skin surface pH of 4.7+/−0.3 for at least 6 hours, at least 8 hours, or at least 12 hours; or between 6 hours and 24 hours.

In an exemplary embodiment, an exemplary composition provided herein may comprise a strong pH buffering capacity at a pH level ranging between 3 to 6.5, which may provide long lasting control over skin surface pH and may prevents skin surface pH fluctuations.

In an exemplary embodiment, an exemplary composition may comprises an acid comprising a plurality of carboxylic acid groups, wherein at least one carboxylic acid group has a pKa around 4.7, at least one carboxylic acid group has a pKa between 4.7 and 6.5, and at least one carboxylic acid group has a pKa between 3.0 and 4.7. In some variations, the composition may further comprise the conjugate base of the acid. In an exemplary embodiment, an exemplary acid may remain charged at around pH 4.7. In an exemplary embodiment, the acid comprises citric acid. In an exemplary embodiment, the composition may comprise citric acid and citrate. In an exemplary embodiment, an exemplary citrate may be sodium citrate. In an exemplary embodiment, an exemplary composition may comprise citric acid, sodium citrate, and gluconic acid. In an exemplary embodiment, an exemplary composition may further comprises gluconate.

In an exemplary embodiment, an exemplary composition may comprise an acid having one carboxylic acid group and its conjugate base, wherein the acid has a pKa of 4.7+/−0.3, and wherein the acid has a molecular weight of at least 140 g/mol. In an exemplary embodiment, an exemplary acid may have a molecular weight between 140 g/mol and 450 g/mol. In an exemplary embodiment, an exemplary acid may comprise ferulic acid.

In an exemplary embodiment, an exemplary composition may comprise a plurality of acids comprising one or more carboxylic acid groups, wherein at least one acid has a pKa around 4.7, at least one acid has a pKa between 4.7 and 6.5, and at least one acid has a pKa between 3.0 and 4.7, and wherein each acid has a molecular weight of at least 140 g/mol. In an exemplary embodiment, exemplary plurality of acids may comprise at least ferulic acid, gluconic acid, or citric acid, or any combination thereof.

In an exemplary embodiment, an exemplary composition comprises a polymer comprising multiple carboxylic acid groups having the pKa in any of the ranges stated above; and/or having a molecular size that prevents its permeation. In some variations, such molecular size is a molecular weight of at least 140 g/mol, or between 140 g/mol and 450 g/mol. In one variation, the composition may comprise a large hydrophilic polymer, such as a carbohydrate that has a pKa in any of the ranges stated above. In such variation, the carbohydrate does not necessarily need to be ionized at pH 4.7 to limit its permeation, as the size will be sufficient to limit its permeation. On the other hand, in another variation, a smaller hydrophilic molecule, such as citric acid benefits from the ionization at pH 4.7 to limit its permeation.

In yet other variations, exemplary composition comprises an acid having at least one chemical group that remains ionized at pH around 4.7. In an exemplary embodiment, an exemplary composition may comprise an acid having at least one chemical group that remains ionized at pH around 4.7; and its conjugate base.

In an exemplary embodiments, an exemplary composition may comprises one or more buffers composed of a high concentration mixture of acids and bases. In certain variations, the acids and bases for the present invention comprise at least one pKa around 4.7 or multiple pKa values between 3 and 6.5.

In an exemplary embodiment, an exemplary composition may comprise a mixture of acids and bases that are both water and lipid-soluble. The water and lipid-soluble characteristics help the mixture of acids and bases to maintain an optimal pH value on the skin surface due to the mixture of water containing a compartment surrounded by lipid sheets on the skin surface.

In an exemplary embodiment, exemplary composition may further include at least one supporting compound capable of accepting at least some hydrogen ions within a pH range between 3 and 5.5. In certain variations, the supporting compound is capable of accepting at least some hydrogen ions within a pH range between 4 and 5. In some variations, the supporting compound decreases skin irritation. In some variations, the composition is capable of maintaining a skin surface pH of 4.7+/−0.3 in the absence of a supporting compound. In some variations, the supporting compound contributes to the capability of the composition to maintain a skin surface pH of 4.7+/−0.3.

In certain variations, a supporting compound is a medium chain fatty acid having a pKa between 4.5 and 5.5. In certain variations of the foregoing, the medium chain fatty acid is caprylic acid, capric acid, or lauric acid, or any combination thereof. In certain variations, a supporting compound is a carbohydrate having a pKa between 3.0 and 4.0. In certain variations of the foregoing, the carbohydrate is hyaluronic acid. In certain variations, a supporting compound is an amino acid having a pKa between 3 and 5. In certain variations of the foregoing, the amino acid is glutamic acid. In one variation, the composition comprises citric acid, gluconic acid, and glutamic acid.

In one embodiment, the composition comprises 3-10% weight for weight (w/w) citric buffer (citric acid/sodium citrate, pKa 3.13, pKa 4.76 and pKa 6.4), 2-6% w/w medium-chain triglycerides (pKa 5.3-4.8), and 0-2% w/w ferulic acid (pKa~4.6). In another embodiment, the composition comprises 5-30% weight for weight (w/w) citric buffer (citric acid/sodium citrate, pKa 3.13, pKa 4.76 and pKa 6.4), 2-6% w/w medium-chain triglycerides (pKa 5.3-4.8), and 0-2% w/w ferulic acid (pKa~4.6).

In some embodiments, the composition further comprises carboxylic acids such as lactic acid, glycolic acid, malic acid, tartaric acid, mandelic acid, tropic acid, salicylic acid, lactobionic acid, glucuronic acid, gluconic acid, ferulic acid, hyaluronic acid, amino acids, or fatty acids, or any combination thereof.

In certain embodiments, the composition may further comprise at least one skin barrier renewal component, at least one anti-inflammatory component, at least one anti-microbial component, at least one humectant, at least one emollient and/or emulsifier, or any combination thereof. In certain variations, at least one skin barrier renewal component comprises a ceramide complex, niacinamide, or phytosphingosine, or any combination thereof. In certain variations of the foregoing, the ceramide complex comprises ceramides, cholesterol, and at least one free fatty acid or a precursor thereof. In certain variations of the foregoing, the ceramides are Ceramide NP, Ceramide AP, or Ceramide EOP, or any combination thereof. In certain variations of the foregoing, the precursor of at least one free fatty acid is sodium lauroyl lactylate. In certain variations of the foregoing, at least one anti-inflammatory and/or anti-microbial component comprises sunflower seed oil, coconut oil, shea butter, or colloidal oatmeal, or any combination thereof. In certain variations of the foregoing, at least one humectant comprises hyaluronic acid, amino acids, glycerin, or xantham gum, or any combination thereof. In certain variations of the foregoing, at one emollient and/or emulsifier comprises caprylic triglyceride, cetearyl alcohol, or ceteareth-20, or any combination thereof.

For example, in certain embodiments, the composition may also contain other ingredients commonly found in cosmetic products such as water, glycerin, ceramides, cholesterol, triglycerides, oils, hyaluronic acid, and/or similar.

In one aspect, provided is a composition comprising: citric acid and sodium citrate, and optionally gluconic acid; a ceramide complex; niacinamide; phytosphingosine; and hyaluronic acid.

In another aspect, provided is a composition comprising: citric acid and sodium citrate, and optionally gluconic acid; a ceramide complex; niacinamide; phytosphingosine; hyaluronic acid; sunflower seed oil; coconut oil; shea butter; and colloidal oatmeal.

In certain embodiments, the acid is present in an amount between 1% and 30% by weight of the total topical composition.

Additionally, the combination of the low pH level and high buffering capacity and ionic strength of the composition provided herein prevents microbial growth. In some embodiments, the composition has no detectable amounts of steroids, added fragrance, sulfates, formaldehyde, alcohol, or added preservatives, or any combination thereof. In one embodiment, the composition is vegan.

Additionally, in some variations, the topical compositions provided include, for example, creams, lotions, serums, cleansers, toners, foundations and/or similar.

Uses of the Topical Formulations

In some embodiments, the compositions provided herein maintain an optimal environment for the key enzymatic reactions involved in skin barrier homeostasis, for instance reactions involving beta-glucocerebrosidase and acid sphingomyelinase. In some variations, the optimal pH and strong pH buffering capacity from the composition are capable of supporting a healthy skin microbiome. As previously mentioned, the low PH level and high ionic strength reduce microbial growth and therefore comprise a self-preserving property.

In some embodiments, the chemical composition provided comprises an optimal pH and strong pH buffering capacity for the treatment of skin barrier function and associated disorders.

In one aspect, provided is a method comprising applying a topical composition to the skin of a human, wherein the skin may have a skin surface pH. In an exemplary embodiment, an exemplary composition consistent with exemplary embodiment may maintain the skin surface pH at around 4.7 for at least 6 to at least 12 hours.

In one aspect, provided is a method comprising applying a topical composition to the skin of a human, for treating skin barrier function and associated disorders. In some variations, the human has a skin disorder. In certain variations of the foregoing, the human has a skin condition resulting from dysregulated skin surface pH.

In certain variations, the human has atopic dermatitis, acne, eczema, psoriasis, rosacea, or xerosis, or any combination thereof. In some variations, applying the topical composition to the skin of the human supports wound healing. In certain variations of the foregoing, applying the topical composition to the skin of the human supports the healing of chronic wounds from diabetes.

In some variations, the human has eczema. In certain variations, applying the topical composition to the skin of the human treats eczema flares, or reduces itch, or a combination thereof. In some variations, applying the topical composition to the skin of the human reduces eczema flare frequency and severity.

In certain embodiments, the chemical composition of the topical application provided is capable of treating skin disorders such as but not limited to different forms of eczema treatment (for example, atopic dermatitis treatment or contact dermatitis treatment), acne treatment, psoriasis treatment, rosacea treatment, xerosis treatment, or similar.

Furthermore, in certain embodiments, the chemical composition of the topical application provided is also capable of treating any skin disorder which results from dysregulated skin surface pH.

It is to be understood that many other possible modifications and variations can be made without departing from the spirit and scope of the invention. Obvious changes, modifications and substitutions may be made by those skilled in the art to achieve the same purpose of the invention.

The exemplary embodiments are merely examples and are not intended to limit the scope of the invention. It is intended that the present invention cover all other embodiments that are within the scope of the appended claims and their equivalents.

In an exemplary embodiment, an exemplary topical composition with an optimal pH buffer capacity at around pH 4.7, may comprise an acid comprising a plurality of carboxylic acid groups. In an exemplary embodiment, at least one carboxylic acid group may have a pKa around 4.7, at least one carboxylic acid group, may have a pKa between 4.7 and 6.5, and at least one carboxylic acid group have a pKa between 3 and 4.7. In an exemplary embodiment, an exemplary composition may have a conjugate base of an exemplary acid.

EXAMPLES

The presently disclosed subject matter will be better understood by reference to the following Examples, which are provided as exemplary of the invention, and not by way of limitation.

Example 1

Skin pH Measurements Using Exemplary Topical Formulation

This example tests an exemplary topical formulation product on human skin by measuring skin pH as follows: 1. Morning skin surface pH; 2. Skin surface pH increase after shower; 3. Skin surface pH recovery after product application-skin pH equilibration at the optimal skin surface pH; and 4. Skin surface pH maintenance over a 5-hour period.

The exemplary topical formulation includes water, citric acid, sodium citrate, glycerin, capric/caprylic triglycerides, cetearly alcohol, ceteareth-20, sodium lauroyl lactylate, hyaluronic acid, ceramide NP, ceramide AP, ceramide EOP, phytosphingosine, and cholesterol.

The topical formulation was applied to the skin on the forearm of a human test subject. The subject was instructed not to wash the skin after product application. The pH was measured 1) before shower, 2) after shower, 3) immediately after product application, 4) 1 hour after product application, 5) 2 hours after product application, 6) 3 hours after product application, 7) 5 hours after product application.

Results are summarized in graph 200 illustrated in FIG. 2A. Based on the results, the use of an exemplary topical formulation, the exemplary topical formulation surprisingly not only corrected elevated pH immediately after product application but also maintained the corrected pH over 5 hours.

FIG. 2A is a graph 200 of the stabilization of the pH skin level after topical application of an exemplary formulation provided herein, consistent with one or more exemplary embodiments of the present disclosure. In detail, respective pH levels over a skin surface are illustrated over time, that is, 1. Morning skin surface pH; 2. Skin surface pH increase after shower; 3. Skin surface pH after production application, and 4. Skin surface pH over a 1, 2, 3, and 5 hour period.

FIG. 2B is a graph 202 comparing an exemplary formulation (solid line with circle markers) to three different topical creams commercially available on the market (dashed lines with square markers) and no product (dashed line with triangle markers) by measuring skin pH, consistent with one or more exemplary embodiments of the present disclosure. In detail, respective pH levels of various products including exemplary formulations are illustrated over a 5 year period.

The three commercially available topical creams tested had a higher than optimal pH and were unable to maintain the skin surface pH at the optimal level.

Example 2

Eczema Treatment Tests

In an exemplary embodiment, exemplary formulations were surprisingly observed to not only help to heal eczema flares and reduce itch, but also provide long term reduction in flare frequency and severity. For example, as discussed previously, with respect to FIG. 3, flare healing is shown after 11 days with respect to the face and after 14 day with respect to the neck.

Additional examples of flare healing are shown in context of FIGS. 5-8 discussed below.

Figure 5:
FIG. 5 illustrates images of a neck area before topical application of an exemplary formulation and seven days after consistent topical application of an exemplary formulation, consistent with one or more exemplary embodiments of the present disclosure.
Figure 6:
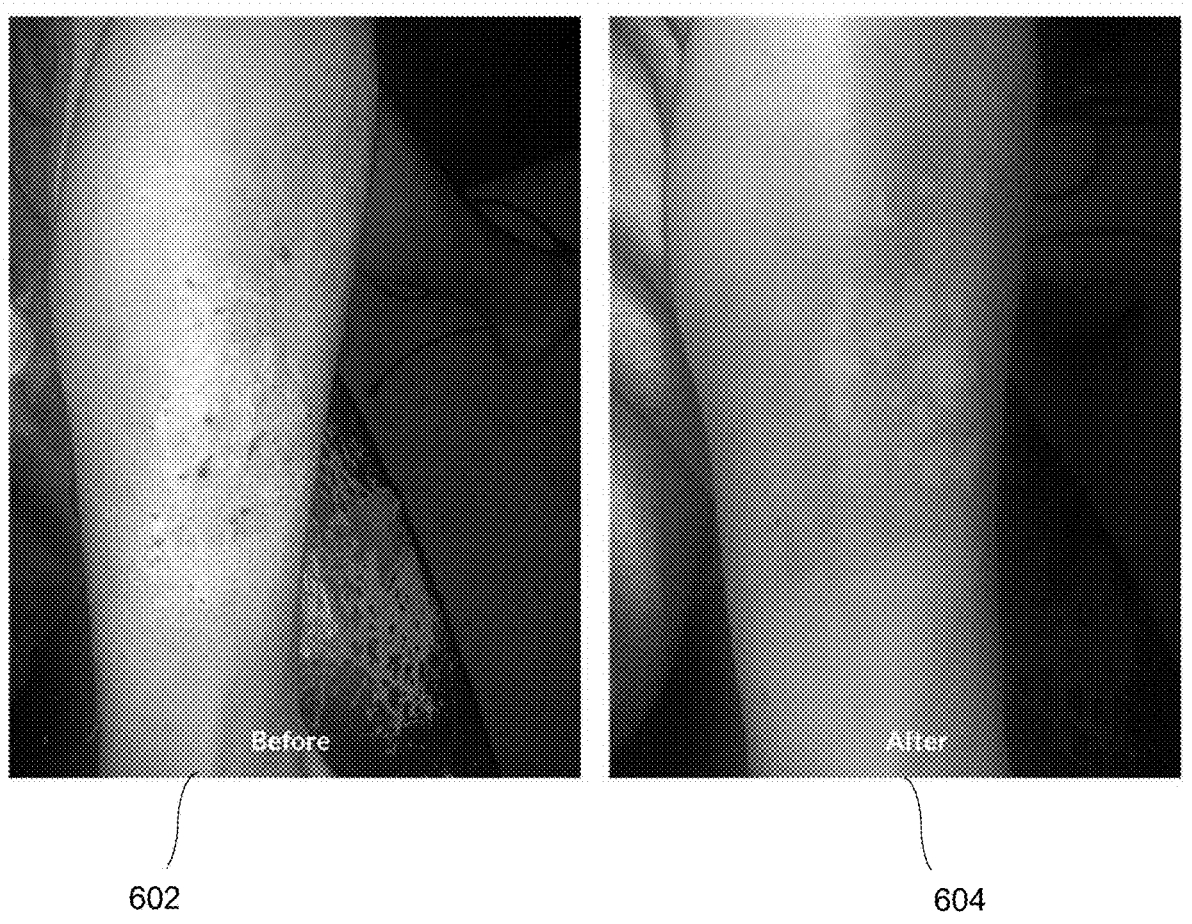
FIG. 6 illustrates images of a shin area before topical application of an exemplary formulation and seven days after consistent topical application of an exemplary formulation, consistent with one or more exemplary embodiments of the present disclosure.
Figure 7:
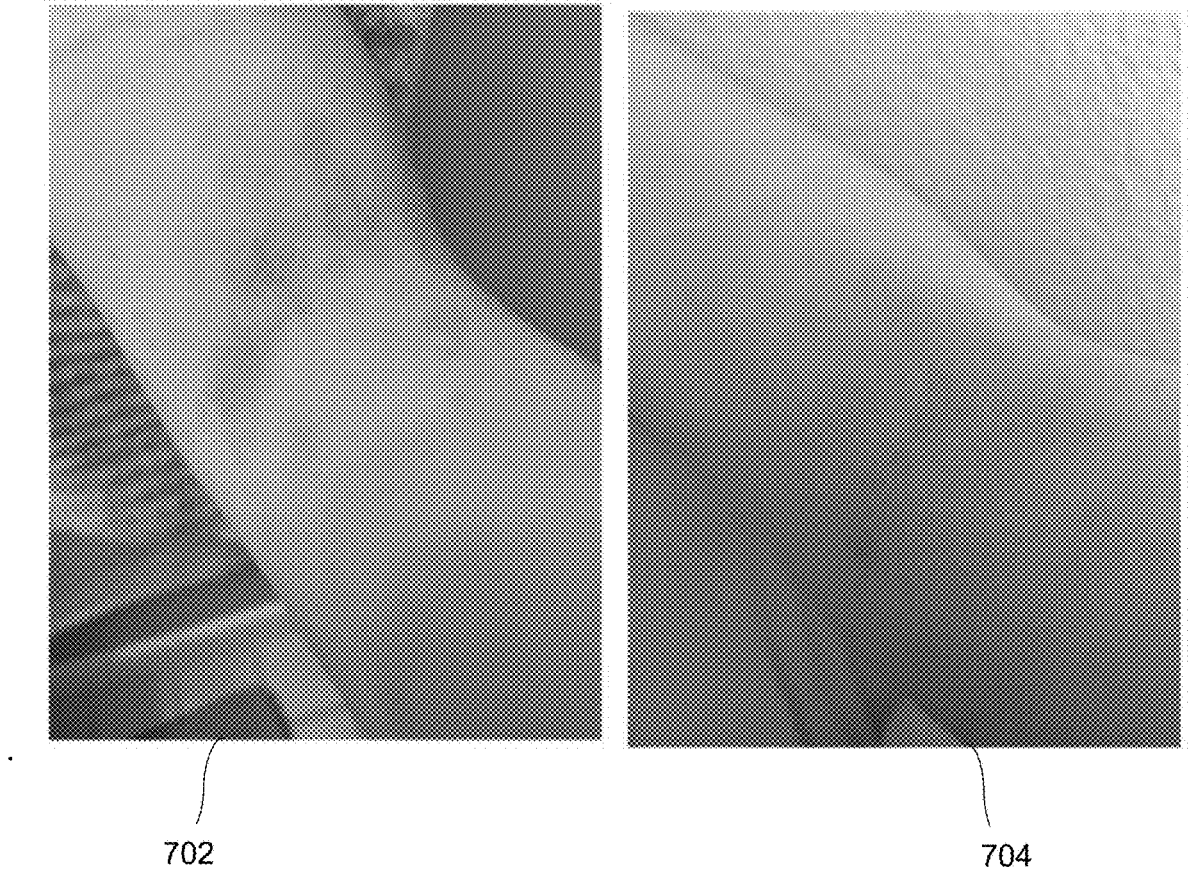
FIG. 7 illustrates images of an area of an arm near the elbow before topical application of an exemplary formulation and fourteen days after consistent topical application of an exemplary formulation, consistent with one or more exemplary embodiments of the present disclosure.

FIG. 5 illustrates images of a neck area before topical application of an exemplary formulation and seven days after consistent topical application of an exemplary formulation, consistent with one or more exemplary embodiments of the present disclosure. In detail, image 502 displays a facial area before topical application of an exemplary formulation while image 504 displays the same facial area from image 502 after seven days of consistent topical application of an exemplary formulation FIG. 6 illustrates images of a shin area before topical application of an exemplary formulation and seven days after consistent topical application of an exemplary formulation, consistent with one or more exemplary embodiments of the present disclosure. In detail, image 602 displays a shin area before topical application of an exemplary formulation while image 604 displays the same shin area from image 602 after seven days of consistent topical application of an exemplary formulation FIG. 7 illustrates images of an area of an arm near the elbow before topical application of an exemplary formulation and fourteen days after consistent topical application of an exemplary formulation, consistent with one or more exemplary embodiments of the present disclosure. In detail, image 702 displays an area of an arm near the elbow before topical application of an exemplary formulation while image 704 displays the same area of the arm near the elbow from image 702 after fourteen days of consistent topical application of an exemplary formulation.

Figure 8:
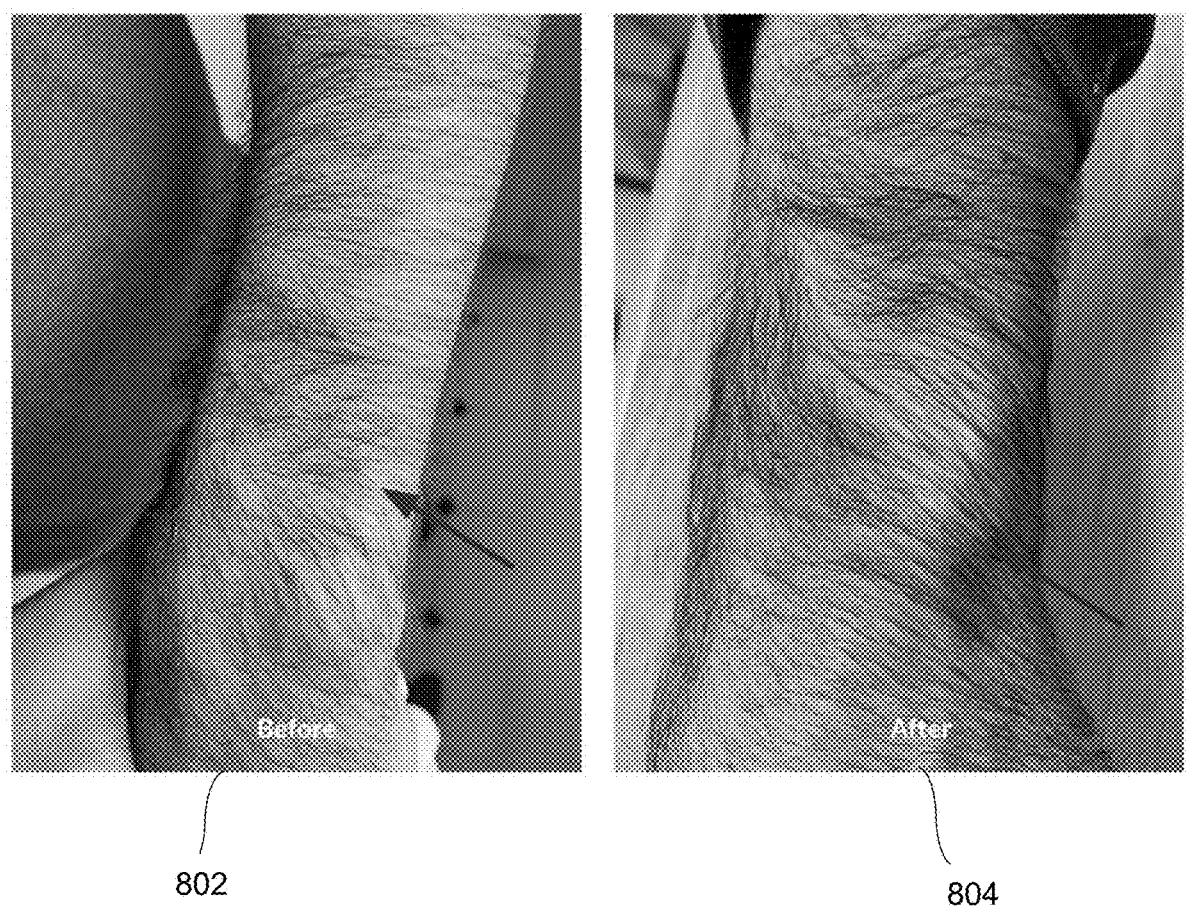
FIG. 8 illustrates images of an area of an arm near the wrist before topical application of an exemplary formulation and fourteen days after consistent topical application of an exemplary formulation, consistent with one or more exemplary embodiments of the present disclosure.

FIG. 8 illustrates images of an area of an arm near the wrist before topical application of an exemplary formulation and fourteen days after consistent topical application of an exemplary formulation, consistent with one or more exemplary embodiments of the present disclosure. In detail, image 802 displays an area of an arm near the wrist before topical application of an exemplary formulation while image 804 displays the same area of the arm near the wrist from image 802 after fourteen days of consistent topical application of an exemplary formulation.

In some cases, such as for the subject initially photographed in the images of FIG. 3, an exemplary formulation was surprisingly found to completely break the eczema cycle, and the subject became eczema free for over 8 months with consistent product application. The exemplary formulation also reduced dependence on topical steroids, and some of the subjects became completely free of eczema flares while using the formulations.

In an exemplary embodiment, exemplary topical formulation used in FIG. 3 comprises water, citric acid, sodium citrate, glycerin, capric/caprylic triglycerides, cetearly alcohol, ceteareth-20, sodium lauroyl lactylate, hyaluronic acid, niacinamide, ceramide NP, ceramide AP, ceramide EOP, phytosphingosine, cholesterol, and xanthan gum.

In an exemplary embodiment, exemplary topical formulation used in FIGS. 5-8 comprises water, citric acid, sodium citrate, glycerin, capric/caprylic triglycerides, cetearly alcohol, ceteareth-20, sodium lauroyl lactylate, hyaluronic acid, niacinamide, ceramide NP, ceramide AP, ceramide EOP, phytosphingosine, cholesterol, and xanthan gum.

Example 3

Skin Surface Correction

This example demonstrates the effect of an exemplary formulation provided herein on skin surface pH after initial pH disruption (due to skin washing with soap and water).

The exemplary topical formulation comprises water, citric acid, sodium citrate, glycerin, capric/caprylic triglycerides, cetearly alcohol, ceteareth-20, sodium lauroyl lactylate, hyaluronic acid, niacinamide, ceramide NP, ceramide AP, ceramide EOP, phytosphingosine, cholesterol, oat, amino acids, and xanthan gum.

The topical formulation was applied to the skin of 2 human test subjects on one forearm and one cheek, and no product was applied to the second forearm, the second cheek, or the nose. The subject was instructed not to wash the skin after product application. The pH was measured 1) before shower, 2) after shower, 3) immediately after product application, and 4) at about 2, 4, 6, and 12 hours after product application.

Figure 4:
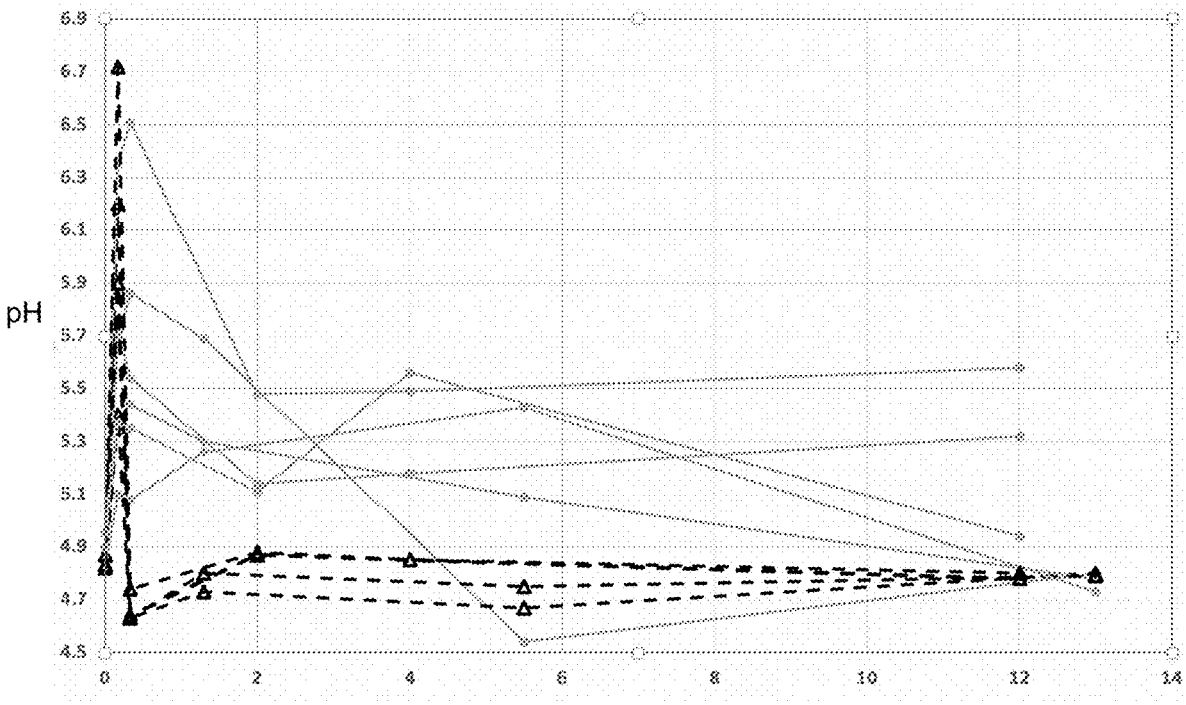
FIG. 4 illustrates a graph showing the effect of an exemplary formulation provided herein on skin surface pH after initial pH disruption (due to skin washing with soap and water). Each solid line is a control without use of the formulation, and each dotted line shows the skin surface pH over 12 hours after application of the exemplary formulation, consistent with one or more exemplary embodiments of the present disclosure.

In an exemplary embodiment, exemplary results are summarized in FIG. 4. In detail, FIG. 4 illustrates a graph 400 showing the effect of an exemplary formulation provided herein on skin surface pH after initial pH disruption (due to skin washing with soap and water). Each solid line is a control without use of the formulation, and each dotted line shows the skin surface pH over 12 hours after application of the exemplary formulation, consistent with one or more exemplary embodiments of the present disclosure.

In an exemplary embodiment, an exemplary formulation applied was surprisingly observed to correct skin surface pH after initial pH disruption (due to skin washing with soap and water) and continue maintaining optimal skin surface pH for over 12 hours. In an exemplary embodiment, by maintaining a desired pH level for over 12 hours, exemplary formulations may maintain a constant pH level for elongated constant periods of time by simply applying them twice daily.

Example 4

Evaluation of Various Buffering Systems

This example evaluates various buffering systems for maintaining a stable pH on human skin over an extended period of time.

Several buffering systems were considered and evaluated:
Lactic acid/lactate in the concentration range 5-30%.
Glycolic acid/glycolate in the concentration range 5-30%.
Lactic acid/lactate/citric acid/citrate in the concentration range 5-30%.
Citric acid/citrate in the concentration range 2-30%.

Citric acid/citrate/gluconic acid/gluconate in the concentration range 2-30%.

In exemplary embodiment, buffering systems comprising small hydroxy acids such as glycolic and lactic acids may be irritating for sensitive skin. In exemplary embodiment, Glycolic and lactic acids also have lower than optimal pKa values, 3.83 and 3.86 respectively. Additionally, glycolic and lactic acids are readily absorbed by the skin, which may provide a challenge for maintaining stable pH over long time periods. On the other hand, Citric acid and gluconic acid are water soluble and may have larger molecular weights, which may limits their skin permeability. They may bee well tolerated on healthy and eczema affected skin. Gluconic acid pKa 3.86 may be too low to provide strong buffer capacity at pH 4.7 on its own. Citric acid may contain three carboxylic groups with pKa 3.13, 4.76, and 6.4, which may be in the desirable pKa range for constructing a pH buffer capable of maintaining a pH range with optimal pH buffering capacity at around pH 4.7 over an elongated period of time. In an exemplary embodiment, citric acid may also remain charged within the optimal skin pH range, which may further limits its skin permeability. In an exemplary embodiment, exemplary steps utilizing two formulation each with a buffer resulting in 4.7 pH levels may be effective and well tolerated.

In an exemplary embodiment, utilizing an exemplary approach with two formulations with different concentrations may allow for maintaining a strong buffer capacity at pH 4.7 without irritating the skin. In an exemplary embodiment, exemplary tolerable buffers may aid in functioning without irritating the skin by addition of supporting molecules that are capable of accepting hydrogen ions within the desirable pH range, such as fatty acids (for example, caprylic acid pKa 4.89, capric acid pKa 4.9, lauric acid pKa 5.3), carbohydrates (such as hyaluronic acid pKa between 3 and 4), ferulic acid pKa 4.61, and amino acids (pKa of the side chains of aspartic acid around 3.65 and glutamic acid 4.25).

In an exemplary embodiment, clinical trials utilizing compositions consistent with exemplary embodiments led to improvements in skin conditions of 100 percent of the test subjects and led to remission and no visible signs of skin conditions in 60 percent of test subjects.

What is claimed is:

1. A composition for treating atopic dermatitis in a target skin area comprising: citric acid and sodium citrate comprising 0.3-15% weight of the composition, gluconic acid comprising 0.1-1.0% weight of the composition, glutamic acid comprising 0.1-1.0% weight of the composition, aspartic acid comprising 0.1-1.0% weight of the composition, and histidine comprising 0.1-2.0% weight of the composition, shea butter comprising 8.5-8.7% weight of the composition,
    the shea butter comprising: oleic acid, stearic acid, palmitic acid, and linoleic acid;
    free fatty acid content of 1% weight of the composition, sunflower oil comprising 6.5% weight of the composition,
    the sunflower oil comprising linoleic acid, and free fatty acid content of 1 percent; and an amino acid, peptide mix, or combination thereof, comprising 0.1-5% weight of the composition;
    wherein the composition maintains the pH of a target skin area between 4.2 and 5.0.

2. The composition of claim 1, wherein the target skin area comprising surface of the skin currently is or previously was affected by eczema symptoms comprising surface of the skin currently or previously indicating the eczema symptoms including one or more of:

redness;

itching;

inflammation;

dryness; and scaling.

3. The composition of claim 1, wherein the composition is capable of maintaining the pH buffer for at least six hours.

4. The composition of claim 1, wherein the composition further comprises:

niacinamide in an amount of 0.5-2% weight;

colloidal oatmeal in an amount of 0.5-5.0-% weight;

glycerin in an amount of 5.0-8.0% weight; and a skin mimicking ceramide complex in an amount of 0.1-5.0% weight.

5. The composition of claim 4, wherein the composition further comprises a solvent in an amount of 53 to 54 weight percentage of the composition.

6. The composition of claim 5, wherein the solvent comprises purified water.

7. The composition of claim 6, wherein the composition further comprises:

niacinamide in an amount of 0.5-2% weight of the composition;

colloidal oatmeal in an amount of 0.5-5.0% weight of the composition;

glycerin in an amount of 5.0-8.0% by weight of the composition; and a skin mimicking ceramide complex in an amount of 0.1-5.0% weight of the composition.

* * * * *